(12) United States Patent
Osterberg

(10) Patent No.: US 7,392,807 B2
(45) Date of Patent: Jul. 1, 2008

(54) FEMALE CONDOM

(76) Inventor: Brian J. Osterberg, P.O. Box 42, Petoskey, MI (US) 49770-0042

( * ) Notice: Subject to any disclaimer, the term of this patent is extended or adjusted under 35 U.S.C. 154(b) by 49 days.

(21) Appl. No.: 11/064,590

(22) Filed: Feb. 24, 2005

(65) Prior Publication Data

US 2005/0194011 A1    Sep. 8, 2005

Related U.S. Application Data

(60) Provisional application No. 60/547,403, filed on Feb. 24, 2004.

(51) Int. Cl.
*A61F 6/06*    (2006.01)
(52) U.S. Cl. .......... 128/830; 128/918
(58) Field of Classification Search .......... 128/830, 128/842, 844, 918
See application file for complete search history.

(56) References Cited

U.S. PATENT DOCUMENTS

| | | | |
|---|---|---|---|
| 4,735,621 A | 4/1988 | Hessel | 604/349 |
| 4,834,113 A | 5/1989 | Reddy | 128/830 |
| 4,840,624 A | 6/1989 | Lee | 604/349 |
| 4,993,433 A | 2/1991 | Reddy | 128/842 |
| 5,094,250 A | 3/1992 | Hessel | 128/844 |
| 5,113,873 A * | 5/1992 | Boarman | 128/830 |
| 5,168,881 A | 12/1992 | Reddy | 128/844 |
| 5,377,692 A | 1/1995 | Pfeil | |
| 5,413,117 A | 5/1995 | Wills | 128/830 |
| 5,490,519 A | 2/1996 | Hessel | 128/842 |
| 5,490,525 A | 2/1996 | Reddy | 128/842 |
| 5,515,862 A | 5/1996 | Artsi et al. | 128/830 |
| 5,535,757 A | 7/1996 | Fleming, Jr. | 128/842 |
| 5,749,862 A | 5/1998 | Lau | 604/353 |
| 2004/0133070 A1 | 7/2004 | Lin | |

FOREIGN PATENT DOCUMENTS

| | | |
|---|---|---|
| DE | 3644344 | 7/1988 |
| EP | 0552814 A1 | 8/1988 |
| EP | 0965314 A1 | 12/1999 |
| GB | 2289224 A | 12/1993 |
| JP | 63234968 A2 | 9/1988 |
| JP | 64-17225 | 1/1989 |
| JP | 01-134836 | 5/1989 |
| WO | 88/05291 | 1/1988 |

\* cited by examiner

*Primary Examiner*—Patricia Bianco
*Assistant Examiner*—Camtu Nguyen
(74) *Attorney, Agent, or Firm*—Gifford, Krass, Sprinkle, Anderson & Citkowski, P.C.

(57) ABSTRACT

An improved female condom apparatus includes a pouch that has a wall, an open end, a closed end and a frame. The frame is positioned proximate the open end of the pouch and extends around a perimeter of the open end. An anchoring device is located within the pouch proximate the closed end to secure the condom in position during use. A harness includes a center strap and may include side straps. One end of each strap is secured to the open end of the pouch. Further, one or more of the straps may be detachable from the pouch. At least the center strap may be constructed of a resilient and/or pliable material. As such, during use the center strap extends between a user's legs and resiliently engages the user's back in a clamping or tensioning action. This clamping action assists in securing the condom in position during use.

17 Claims, 3 Drawing Sheets

FEMALE CONDOM

CROSS-REFERENCE TO RELATED APPLICATIONS

This application claims priority from U.S. provisional patent application No. 60/547,403, filed Feb. 24, 2004.

BACKGROUND OF THE INVENTION

1. Field of the Invention

The present invention concerns an improved female condom. More particularly, the invention concerns a female condom having resilient strap and/or a harness/G-string type assembly. The harness or a portion thereof is operable to provide a clamping action against the body of the user when in use to assist in securing the condom to the user during intercourse.

2. Reference to Related Art

Disclosed in the prior art are a variety of female condoms having a G-string or similar harness assembly for use in securing a condom to the user. For example, International Publication No. WO 88/05291 discloses a barrier device that includes a continuous impermeable shield member shaped and dimensioned so that, in operation, it covers the entrance of a user's vagina. Integral with the shield member is a continuous, impermeable, flexible pouch arranged to receive a penis and to be introduced into the vagina to form a liquid barrier between the penis and vagina. The shield and pouch may be secured in an operational position by straps that pass around the hips and between the buttocks to form a G-string type garment. Alternatively, the membrane may be secured in the operational position in a panty-like garment.

In another example, U.S. Pat. No. 5,168,881 (see also U.S. Pat. No. 5,490,525) to Reddy discusses a prophylactic device. The device includes a hollow pouch that has a closed end and an open end. The open end of the pouch is attached to and surrounded by a continuous flange member. The flange extends outwardly at least one inch around the open end of the pouch. The flange must be liquid impermeable and may be flexible or nonflexible and elastic or nonelastic. A plurality of straps are secured to the flange that are connected at their opposite ends to bands that may be worn around the waist or around the pelvic region of the female person using the device. In another embodiment, the device is connected to a bikini-like panty garment having an elastic waist portion.

Absent from the prior art is a female condom having a harness assembly that is operable to provide a clamping action to assist in securing the condom to the user.

SUMMARY OF THE INVENTION

The present invention concerns an improved female condom that includes a condom and a harness. The condom includes a pouch that has a wall that defines an open end, a closed end. A frame may also be provided proximate the open end. Specifically, if present, the frame is positioned proximate the open end of the pouch and it extends around a perimeter of the open end.

An anchoring device, such as a flexible disc is positioned within the pouch proximate the closed end. In operation, when the pouch is inserted in a user's vagina, the anchoring device causes the wall of the pouch to press against the vaginal wall and thereby reduce the possibly of accidental removal of the pouch during use.

The harness includes a resilient center strap and may include a resilient first side strap and a resilient second side strap. Each of the straps have a first end secured to the closed end (or the frame) of the pouch and seconds end opposite the first end that are secured together.

In operation, at least the center strap extends from the open end of the pouch, between the legs and buttocks of the user to resiliently engage the user's back. As such, the strap aids in securing the pouch in position during use.

The condom has a hollow pouch with an open end and a closed end. The harness includes straps that are secured to the open end of the pouch and secured together at there opposite ends. One or more of the straps are formed such that it is "springloaded" or otherwise provides a resilient tension against a user when in use to further assist in securing the condom in position during use. For example, the straps may be formed with an arc or U-shape using materials such a polymer or an insulated (or otherwise covered) wire. In a particularly preferred example, the center strap is constructed as a pliable but resilient arc using a polymer material known in the art. In the operation, the user wears the harness of the condom like a G-string and inserts the pouch into the user's vagina. Once in position the resilient nature of the strap will cause the strap to push against the "small-of-the-back" of the user in a clamping action that holds the strap and thus the condom in position during intercourse.

BRIEF DESCRIPTION OF THE DRAWINGS

Reference will now be made to the attached drawings wherein like reference numbers refer to like parts throughout and wherein.

DETAILED DESCRIPTION

Figure 1:
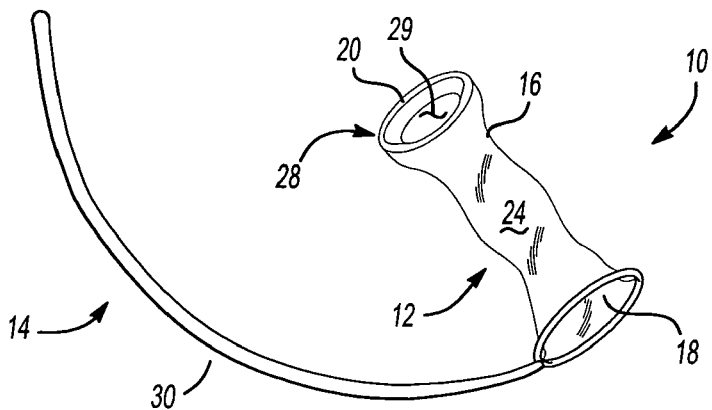
FIG. 1 is a perspective view of the improved condom of the present invention.

Referring now to FIGS. 1, the improved female condom 10 assembly of the present invention includes a condom portion 12 and a harness 14. The condom portion 12 includes a pouch 16 having wall 24 that defines an open end 18 and a closed end 20. The harness 14 may include one or more a strap(s) that is secured to the open end 18 of the pouch 16 and may be secured together at there opposite ends (as discussed below). The pouch 16 is operable to be introduced into a user's vagina (not shown) to form a barrier to fluids between a penis and the vagina. The harness 14 portion of the assembly 10 is worn by user to assist in maintaining the pouch 16 in position during use.

Figure 2:
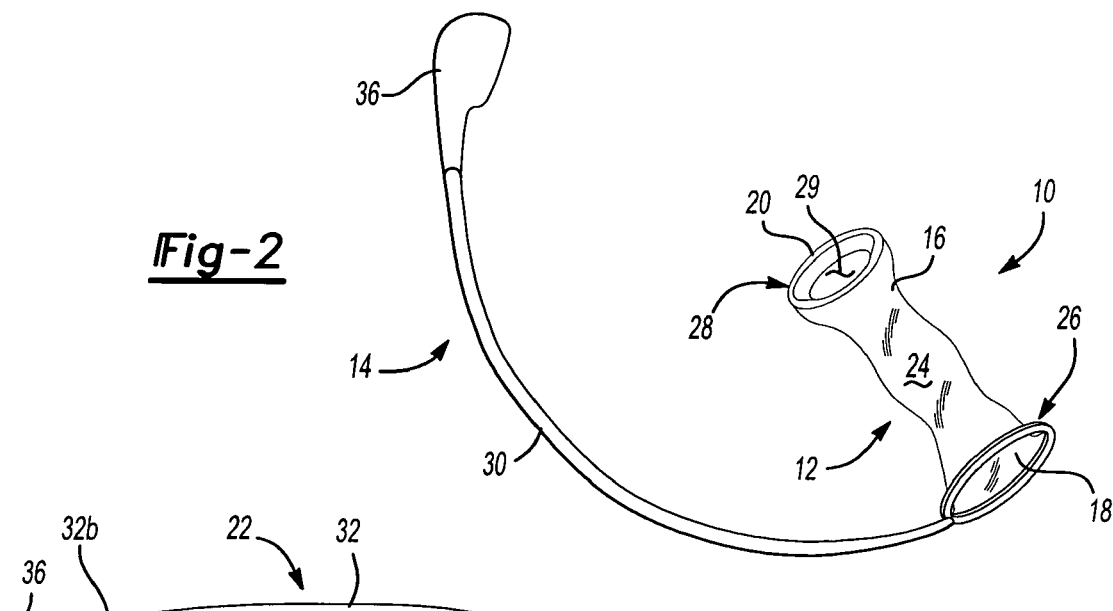
FIG. 2 is a perspective view of another embodiment of the improved condom of the present invention.

Referring to FIGS. 1 and 2, the pouch 16 of the condom 12 includes a wall 24 that may be constructed of a continuous, water impermeable, flexible material such as latex, organic materials, and a polymer(s) or any other material known in the art. A frame 26 may be positioned on or within the wall 24 of the pouch 16 proximate the open end 18 and preferably around the perimeter thereof. The frame 26 may be constructed in a variety of configurations including: as a single flexible ring; as a single rigid ring; from two or more rigid or flexible elements disposed within pockets or piping surrounding the perimeter of the open end 18; or as a collar, collarette or flange (discussed below) that surrounds and extends away from the perimeter of the open end 18. The frame 26 may also be formed such that the open end 18 assumes a particular shape (e.g., a circle, triangle (v-shape), square, oval, rectangle, star, etc.). The condom 10 of the present invention may also be constructed without a frame 26.

As shown in FIGS. 1-5, an anchoring device 28, such as a flexible disc or sponge 29 is secured within the pouch 16 proximate the closed end 20. In operation, when the pouch 16 is inserted in a user's vagina (not shown), the anchoring device 28 causes the wall 24 of the pouch 16 to press against the vaginal wall and thereby reduce the possibly of accidental removal of the pouch 16 during use. The anchoring device 28 may be constructed of a sponge or sponge-like material, a polymer, a non-porous material, a non-sponge material or any other material known in the art. Furthermore, the anchoring device 28 may be constructed in different shapes (circle, oval, square, rectangle, etc) and sizes.

Figure 3:
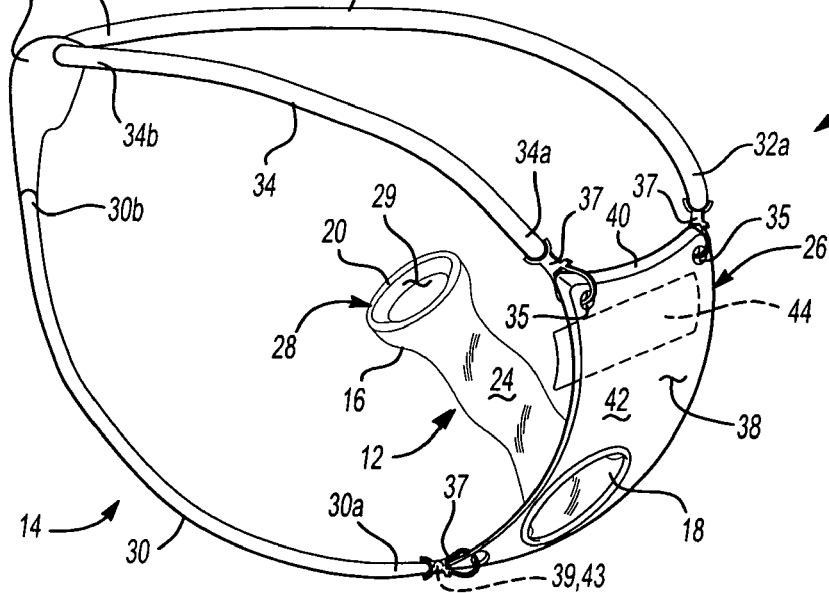
FIG. 3 is a perspective view of yet another embodiment of the improved condom of the present invention including a flange and eyelets.
Figure 4:
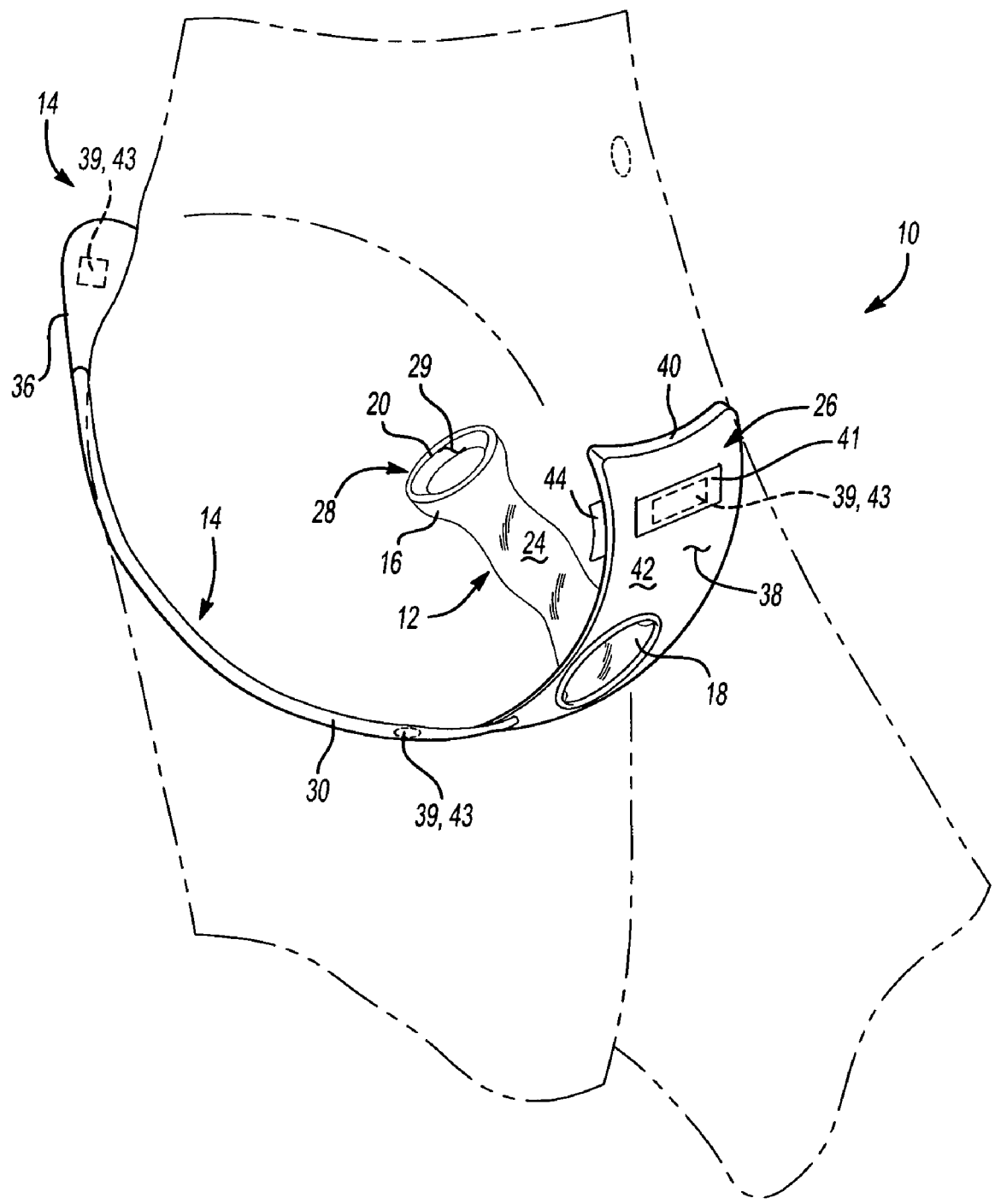
FIG. 4 is a perspective environmental view of still another embodiment of the improved condom of the present invention.
Figure 5:
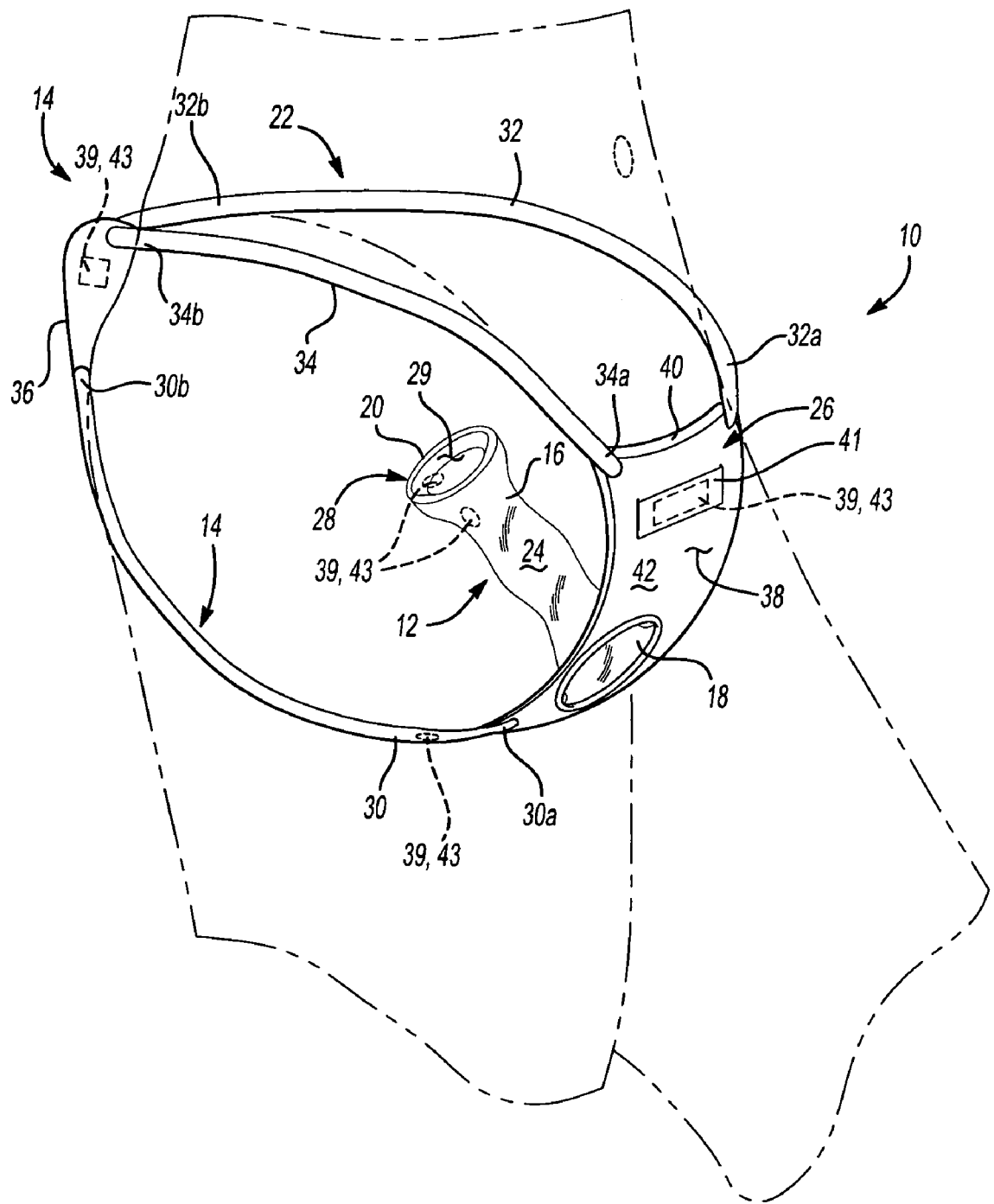
FIG. 5 is a perspective view of a final embodiment of the improved condom of the present invention.

Referring to FIGS. 3-5, the harness 14 may include a center (or first) strap 30 and a pair (or a first and second) of side straps 32, 34. The center strap 30 has an end 30a that is secured to the open end 18 of the pouch 16. However, if the pouch 16 includes a frame 26, the end 30a of the center strap 30 may be secured to a portion of the frame 26. For example, where the frame 26 has a triangle (or v-shaped) shape (see e.g., FIG. 3), the end 30a of the center strap 30 may be secured to the frame 26 at an apex of one corner of the frame 26. The other end 30b of the center strap 30 may include a connecting member 36.

Still referring to FIGS. 3-5, the pair of side straps 32, 34 are also each secured at one end 32a, 34a to the open end 18 or, alternatively, the frame 26 of the open end 18 of the pouch 16. In the absence of a frame 26 the ends 30a, 32a, 34a of the straps 30, 32, 34 are secured to the perimeter of the open end 18. Eyelets 35 may also be provided along the perimeter of the open end 18 or may be defined by the frame 26 as a means to attach the straps 30, 32, 34 to the condom portion 12. The opposite or other ends 32b, 34b of the side straps 32, 34 may be secured to or be formed integral with the other end 30b of the center strap 30 or the connecting member 36.

It will be appreciated that the center strap 30 may be positioned between a user's legs and buttocks and that the side straps 32, 34 may be positioned around a user's waist such that the harness 14 as described has the appearance of a G-string garment with the other ends 30b, 32b, 34b of the straps 30, 32, 34 being secured (as described above) in the region of the lower back of a user.

Referring to FIGS. 1-5, one or more of the straps 30, 32, 34 are formed such that it is "spring loaded" or otherwise provides a resilient tension against a user when in use to further assist in securing the condom 10 in position during use. For example, the straps 30, 32, 34 may be formed or molded into an arc or U-shape using materials such a polymer or an insulated (or otherwise covered) wire of suitable gage. Accordingly, it will be appreciated that the straps 30, 32, 34 may be constructed such that the straps 30, 32, 34 may be rigid, pliable, flexible or a combination thereof. The straps 30, 32, 34 may be constructed in a pre-stressed or shaped manner such that the straps conform (or hug) to particular body shapes (i.e., hips, waist, between the buttocks, etc.). The straps 30, 32, 34 may also be constructed of a glow-in-the-dark material or otherwise configured to glow in the dark (e.g., reflectors, lights, etc.). As will be further discussed below, the straps 30, 32, 34 may also be detachable.

As shown in FIG. 4 and 5, the center strap 30 may be constructed as a pliable arc using a polymer material known in the art. As such, in operation, if the distance between the ends 30a, 30b of the strap 30 is insufficient to position the center strap 30 between a user's legs, the user may manually widen the strap 30. Thereafter, the user wears the harness 14 of the condom 10 as a G-string (See FIG. 5) and inserts the pouch 16 into the user's vagina. Once in position, the resilient nature of the strap 30 will push against the back (preferably the "small-of-the-back") of the user in a clamping action to assist in holding the strap 30 and thus the condom 10 in position during intercourse.

As shown in FIGS. 1, 2 and 4, the assembly 10 of the present invention may be constructed using only a single strap. For example, the center strap 30 may be a rigid, pliable, flexible or combination member that is constructed such that it extends from the open end 18 of the condom portion 12, between the user's legs and buttocks and pushes against the user's back in a clamping action. Further, the side straps 32, 34, if present, may be constructed such that those straps 32, 34 are detachable (as shown in FIG. 3) from the condom portion 12. As shown in FIG. 3, the center strap 30 may also be designed to be detachable such that the entire harness 14 assembly may be reused. Accordingly, the entire harness 14 may constructed as a separate unit apart from and connectable to the pouch 16. Specifically, in such an embodiment, a releasable clip 37 (or like clasping device) is disposed at the end 30a, 32a, 34a of each strap 30, 32, 34. The clip(s) 37 are operable to engage the frame 26 (or, alternatively the wall 24 where there is no frame 26) of open end 18 of the pouch 16.

Referring to FIGS. 1 and 2, to provide additional comfort to the user of the present invention, the connecting member 36 at the other end 30b of the strap 30 may be constructed as a triangular shaped ring, enclosed circle or oval, or as a contoured shape body conforming shape. The connecting member 36 functions to distribute the clamping action of the strap(s) 30, (32, 34) to a wider area of the user's back and also provides greater comfort for the user.

As shown in FIGS. 4 and 5, the condom 10 assembly may also include a stimulation device. Specifically, condom 10 assembly may include a stimulation device that is electronically charged to pulsate or vibrate causing the condom portion 12 to do the same by virtue of being connected to, for example, the straps 30, 32, 34. More particularly, the stimulation device may include one or more microchip controlled vibration or pulsing devices 39 that may be positioned on the wall 24 of pouch 16 of the condom 12, at any point along one or more of the straps 30, 32, 34, at the connection point of the straps 30, 32, 34, on, in or in proximity to the eyelets 35, on a clip(s) 37, on or in the connecting member 36, in or on the anchoring device 28 and/or (as described below) on the frame 26. Preferably, the device 39 induces or transmits a pulsation and/or vibration to one or more of the straps 30, 32, 34 that is communicated to the condom portion 12 (including the frame 26 thereof). The microchip controlled vibration or pulsing devices 39 may be powered using e.g., an on-chip, microbattery, commercially available kinetic motion technology, hearing aid batteries or similar size batteries mounted on in proximity to the device 39 or the like. Examples of such kinetic motion power generating sources are disclosed in U.S. Pat. Nos. 5,822,278 and 6,154,422 to the Seiko Epson Corporation, the disclosures of which are incorporated by reference herein. As an alternative (or in addition) to the vibration or pulsing device 39, the stimulation device may also include or comprise a chemical or electronic heating element 43, such as a heater chip, thin film heating element, micro-fibers integrated into one or more elements/structures of the condom 10 assembly or a known exothermic agent or similar known chemical agent that create the sensation of heat. One or more heating elements 43 also may be positioned on the condom 10 along with, or in place of, a vibration or pulsing device 39 at any point where a vibration or pulsing devices 39 might also be positioned as described above. Further, the heating element 43 may be powered (if necessary) using the same or similar means described above for use in connection with the vibration or pulsing devices 39. The motion and/or heat of the condom 10 assembly thus provides added stimulation to the female wearer of the condom, as the vibration and/or heating sensation is felt on the female sex organs.

Still referring to FIGS. 4 and 5, alternatively, or additionally, the microchip controlled vibration or pulsing device 39 may be positioned on or connect to the frame 26. For example, the device 39 may be disposed within a pocket 41 on the frame 26 or that is disposed within the wall 24. Where the frame 26 is a flange or collar, the pouch 16 may be disposed on the side of the frame 26 that faces the user or the side of the frame 26 that faces away from the user. The device 39 may be associated with a wire (or a wire frame 26) that extends through the frame 26 and that is cause to vibrate, etc, upon activation of the device.

Referring to FIGS. 3-5, the open end 18 of the pouch 16 may include a continuous flange member 38. As set forth above, the flange 38 may be constructed such that it extends outwardly from the open end 18 of the pouch 16 between one and four inches, depending on the needs of the user. The flange 38 may also function as the frame 26 (see e.g., FIG. 3). The flange 38 has an interior surface 40 that faces toward the user when the condom 10 is in use and an exterior surface 42 that faces away from the user when the condom 10 is in use. The flange 38 extends outwardly around the perimeter of the open end 18 of the pouch 16 and may be constructed of a flexible or nonflexible and elastic or nonelastic material. Preferably, the flange 38 is impermeable to liquid.

Referring now to FIG. 4, a pad 44 may be position on the interior surface 40, exterior surface 42 or both surfaces 40, 42 of the flange 38 (frame 26). The pad 44 may be sponge. The pad 44 may also be impregnated or otherwise coated with a spermacide.

Having thus described my invention, various other embodiments will become apparent to those having skill in the art that do not depart from the scope of the claims or equivalents thereof.

I claim:

1. An improved female condom apparatus comprising:
   a pouch having a wall that defines an open end and a closed end and plurality of eyelets proximate the open end of the pouch;
   an anchoring device secured within the pouch proximate the closed end; and
   a harness including a resilient center strap a first side strap and a second side strap, the center strap having a first end secured to the open end of the pouch and a second end opposite the first end, the first and second side straps having first ends secured to the open end of the pouch and second ends secured to the second end of the center strap, and each strap having a clip positioned on the first end thereof, each clip being operable to be detachably secured to one eyelet of the plurality of eyelets; and
   a powered stimulation device;
   whereby during use the center strap is operable to be extend from the open end of the condom and between a user's legs such that the second end of the center strap will resiliently engage a user's back to aid in securing the pouch in position.

2. The improved female condom apparatus of claim 1, further comprising a frame positioned proximate the open end of the pouch and extending around a perimeter of the open end of the pouch.

3. The improved female condom apparatus of claim 2, wherein the frame comprises a flange.

4. The improved female condom apparatus of claim 1, further comprising a flange positioned proximate the open end of the pouch, the flange having an interior surface and an exterior surface.

5. The improved female condom apparatus of claim 4, further comprising a pad positioned on the interior surface of the flange.

6. The improved female condom apparatus of claim 5, wherein the pad comprises a spermacide.

7. The improved female condom apparatus of claim 4, further comprising a pad positioned on the exterior surface of the flange.

8. The improved female condom apparatus of claim 7, wherein the pad comprises a spermacide.

9. An improved female condom apparatus comprising:
   a pouch having a wall that defines an open end and a closed end;
   an anchoring device secured within the pouch proximate the closed end; and
   a harness including a resilient center strap, the strap having a first end secured to the open end of the pouch and a second end opposite the first end; and
   a powered stimulation device comprising a vibration device positioned at the second end of the center strap;
   whereby during use the center strap is operable to be extend from the open end of the condom and between a user's legs such that the second end of the center strap will resiliently engage a user's back to aid in securing the pouch in position.

10. The improved female condom apparatus of claim 9, wherein the powered stimulation device comprises a battery powered stimulation device.

11. The improved female condom apparatus of claim 9, wherein the powered stimulation device comprises a kinetic energy powered stimulation device.

12. The improved female condom apparatus of claim 9, wherein the powered stimulation device comprises a beating element.

13. The improved female condom apparatus of claim 12, wherein the heating element comprises a chemical heating element.

14. The improved female condom apparatus of claim 12, wherein the heating element comprises an electronic heating element.

15. The improved female condom apparatus of claim 9, wherein the powered stimulation device comprises a microchip controlled vibration device.

16. The improved female condom apparatus of claim 9, wherein the powered stimulation device comprises a pulsing device.

17. The improved female condom apparatus of claim 16, wherein the powered stimulation device comprises a microchip controlled pulsing device.

* * * * *